United States Patent [19]

Bierman

[11] Patent Number: 4,711,636
[45] Date of Patent: Dec. 8, 1987

[54] CATHETERIZATION SYSTEM

[76] Inventor: Steven F. Bierman, 143 Eighth St., Del Mar, Calif. 92014

[21] Appl. No.: 796,301

[22] Filed: Nov. 8, 1985

[51] Int. Cl.⁴ .............................................. A61M 5/00
[52] U.S. Cl. .................................... 604/180; 604/283; 128/DIG. 26
[58] Field of Search ............... 604/180, 174, 164, 165, 604/177, 178, 179, 280, 283; 128/DIG. 26

[56] References Cited

U.S. PATENT DOCUMENTS

| | | |
|---|---|---|
| 3,064,648 | 11/1962 | Bujan . |
| 3,766,915 | 10/1973 | Rychlik . |
| 3,906,946 | 9/1975 | Nordstrom . |
| 3,920,001 | 11/1975 | Edwards . |
| 3,973,565 | 8/1976 | Steer . |
| 4,082,094 | 4/1978 | Dailey ..................... 128/DIG. 26 X |
| 4,114,614 | 9/1978 | Vargas . |
| 4,129,128 | 12/1978 | McFarlane .............. 128/DIG. 26 X |
| 4,250,880 | 2/1981 | Gordon ................... 128/DIG. 26 X |
| 4,316,461 | 2/1982 | Marais et al. ......................... 604/179 |
| 4,326,519 | 4/1982 | D'Alo et al. ..................... 604/177 X |
| 4,362,156 | 12/1982 | Feller et al. ..................... 604/177 X |
| 4,449,975 | 5/1984 | Perry . |
| 4,474,559 | 10/1984 | Steiger . |
| 4,516,968 | 5/1985 | Marshall et al. . |

FOREIGN PATENT DOCUMENTS 2341297  3/1975  Fed. Rep. of Germany ...... 604/180

Primary Examiner—Stephen C. Pellegrino
Attorney, Agent, or Firm—Knobbe, Martens, Olson & Bear

[57] ABSTRACT

A catheterization system is comprised of an anchoring pad permitting one-time attachment to a patient, a catheter, and a tubing adaptor. The catheter is mounted on the anchoring pad in order to prevent lateral or longitudinal movement with respect to the patient, thereby preventing injury. The tubing adaptor is connected to the catheter so as to absorb rotational forces applied to the adaptor by incidental movement in the IV tubing. The adaptor/catheter engagement is rendered secure against longitudinal removal forces by means of a spring-actuated latch extending distally from the adaptor and interengageable with a reduced diameter neck portion on the catheter. The anchoring pad is also provided with means for receiving the safety loop in the IV tubing. A method associated with this catheterization system is also disclosed.

20 Claims, 5 Drawing Figures

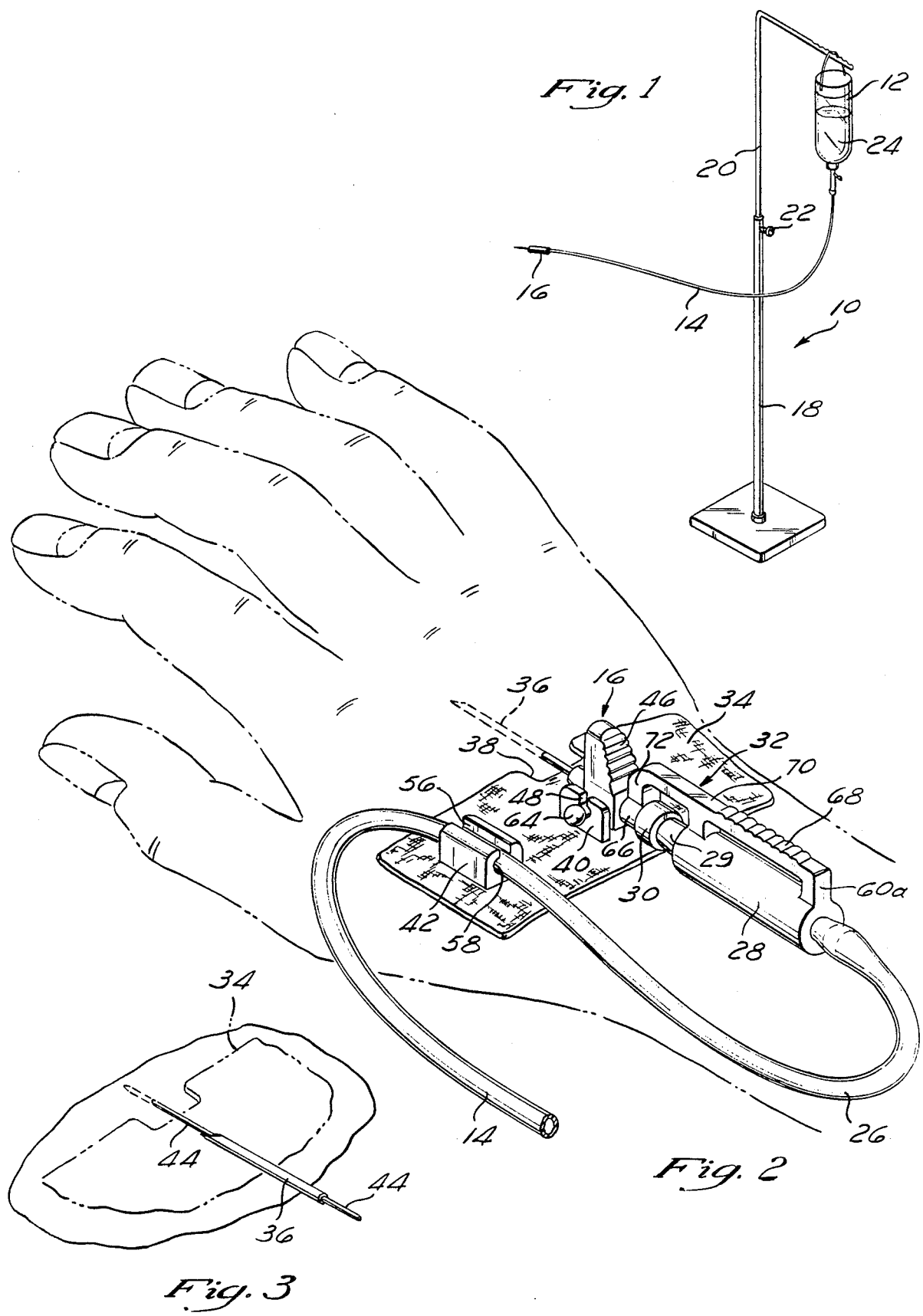

CATHETERIZATION SYSTEM

BACKGROUND OF THE INVENTION

The present invention relates to a percutaneous catheterization system, and, more particularly, to a system which facilitates the frequent replacement of the catheter tubing which is necessary in such catheterization procedures.

It is very common in the treatment of hospitalized patients to utilize intravenous (IV) catheters to introduce certain fluids directly into the bloodstream of the patient. Such procedures are also becoming more common outside of the hospital as the high cost of hospital medical care has brought about the advent of neighborhood out-patient clinics and home health care.

In IV catheterization, a supply of fluid is maintained in a container which is located at a height higher than the patient. The catheter tubing flows from the supply container to the location of introduction into the patient where it is attached to a catheter. This location is typically the back of the patient's hand or a vessel on the inside of the arm. Typically, a needle or other stylet is first introduced through the cannula portion of the catheter and into the skin of the patient at the desired location, and then removed after the cannula is inserted into the skin. The fluid then flows directly into the blood vessel of the patient by gravity, or, if necessary, by the pressure generated by the head of the fluid above the height of the patient In common practice, the catheter is maintained in place on the skin of the patient by the use of adhesive or surgical tape. Likewise, the connection between the tubing and the catheter is also maintained by use of tape. In addition, a safety loop is typically formed in the tubing so that any tension applied to the tubing is not passed directly to the cannula of the catheter but is taken up in the slack of the safety loop. This loop is also typically taped loosely to the skin of the patient. This entire taping procedure takes several minutes of the valuable time of a nurse.

IV catheterization is frequently maintained for several days, depending upon the condition of the patient. This longevity requirement gives rise to several problems associated with IV catheters. For example, the catheter tubing must be replaced every 24 to 48 hours in order to maintain the sterility of the fluid and the free-flow of the fluid through the tubing. Thus, a nurse is often called upon to frequently change the tubing and to retape the connection. Furthermore, the taping of the catheter to the skin of the patient often covers the location of insertion of the cannula. Thus, the tape must be removed in order to inspect the insertion location for inflammation or infection. A complete new taping procedure must then be followed. In short, a great deal of valuable time of the nurse is wasted in applying significant amounts of surgical tape to IV catheters. Furthermore, the frequent application and removal of surgical tape often results in the excoriation of the skin in the area of the insertion.

Mechanical connections designed to avoid the use of tape have not proven to be satisfactory. Typically, such connections are threaded, resulting in the twisting of the tubing. The connections are also bulky and heavy, and are not preferred by nurses.

SUMMARY OF THE INVENTION

The present invention fills the need in the prior art by providing a system for facilitating the changing of the catheter tubing without the attendant problems associated with the prior art. The system comprises an anchoring pad having a self-adhesive backing for simple, secure attachment of the system to the skin of the patient, a specially designed catheter, and a tubing adaptor having a spring-actuated retention latch for connecting the IV tubing to the catheter. These components can be quickly and easily connected, and re-connected, without the need of surgical tape or other awkward, time-consuming procedures.

The anchoring pad of the present invention provides an important advantage in that it permits the convenient attachment of the present catheterization system to the skin of the patient while avoiding the necessity of frequent re-attachment when changing the IV tubing. Once the anchoring pad is in position on the patient, either on the back of a hand or on the arm, the tubing may be changed as frequently as necessary without removing the pad. Even the catheter itself can be easily detached from the anchoring pad and replaced, if necessary, or its point of insertion changed due to infection which may result around the original point of insertion.

The anchoring pad is provided with a self-adhesive backing material which adheres to the skin without excoriation. Mounted on the anchoring pad is a bridge consisting of a pair of upright members having slotted openings in the top sides thereof for receiving the attachment of the catheter. Just in front of the bridge is a cut-out portion in the anchoring pad which serves to identify the approximate location for the catheter insertion while at the same time permitting a visual inspection of that location in order to detect infection.

Also on the pad is mounted a slotted member for receiving the catheter tubing formed in a safety loop configuration. As explained above, near the location of the catheter insertion, a safety loop is formed in the catheter tubing so that any tension or pressure inadvertently placed on the tubing will not be directly transmitted to the catheter. Rather, it will be taken up in the slack of the loop. The slotted member provides a convenient mechanism for forming the loop and attaching it to the patient. The friction fit between the tubing and the slotted member is such that the tubing is not permitted to slide easily through the slotted member, thus providing the necessary degree of safety to the patient.

The catheter of the present invention is also uniquely designed to facilitate insertion and utilization of the anchoring pad and tubing adaptor. Preferably, the catheter is manufactured from a biologically-compatible polymer material which is small, lightweight, and easy to handle. To this end, the catheter is also provided with a finger-press member to facilitate insertion of the catheter into the skin of the patient and to guide it into position. Typically, the catheter is provided with a Teflon (a trademark of DuPont) cannula which is inserted into the skin of the patient. The patient's vessel is first cannulated with a needle, and the cannula on the catheter is then inserted into the patient over the needle. After insertion of the cannula, the needle can then be removed, leaving the catheter in place.

The catheter is also provided with a pair of lateral arms for attachment to the anchoring pad. At the end of each lateral arm is an enlarged end which prevents the lateral movement of the catheter on the anchoring pad.

The arms can be easily press-fit into the bridge associated with the anchoring pad in order to hold the catheter in place adjacent the skin of the patient, thus obviating the need for surgical tape or other time-consuming procedures. The fit between the lateral arms of the catheter and the bridge of the anchoring pad is such that only a modest amount of pressure is necessary in order to accomplish engagement and disengagement. This pressure is applied in a direction transverse to that of the cannula in order to avoid pain or injury to the patient. The enlarged ends on the lateral arms prevent lateral movement of the catheter which is an important advantage of the present invention since such movement could also cause damage to the skin of the patient at the point of insertion. Alternatively, if an anchoring pad is not used, the lateral arms can be used for direct suture to the skin.

The catheter is also provided with a proximal cuff for direct attachment of the tubing adaptor. The cuff is nondirectional such that any orientation of the adaptor with respect to the cuff is tolerated without resulting in the twisting of the tubing. Just distal of the cuff is a neck of reduced diameter for receiving the latch on the tubing adaptor in order to retain the adaptor in place.

The tubing adaptor is comprised of a handle-like body to facilitate the handling of the adaptor by the nurse. The body is substantially cylindrical having a conical distal end for friction engagement with the cuff on the proximal end of the catheter. This engagement is rotationally non-sensitive such that any twisting of the tubing is not communicated to the catheter. The proximal end of the adaptor is likewise provided with an opening in order to receive the catheter tubing. Preferably, the tubing is integrally connected to the adaptor in the molding process.

In order to provide for the secure attachment of the adaptor to the catheter, the former is provided with an forwardly-extending, spring-actuated latch which engages the reduced diameter neck portion of the catheter. The leading edge of the latch is tapered to facilitate engagement of the adaptor with the cuff of the catheter. In other words, as the conical distal end of the adaptor is mated into the cuff on the catheter, the tapered leading edge of the latch engages the exterior periphery of the cuff, forcing the latch to lift up. After the engagement is complete, the latch will be adjacent the reduced diameter neck portion on the catheter. The resilient spring bias in the latch will cause it to snap down into the neck and remain there, thus securing the connection. Thus, any longitudinal forces tending to cause the tubing or adaptor to be removed from the catheter will be resisted by the interference engagement between the latch and the distal end of the cuff.

The latch is cantilevered from its mounting position at the forward portion of the adaptor body, thus providing a degree of resiliency and flexibility. The latch activator is supported at each end, and is preferably integral with the latch. Thus, manual pressure applied to the activator will cause the latch to lift up by pressing on the actuator in order to clear the outer periphery of the cuff. A removal force can then be exerted on the adaptor in order to remove it from the catheter, if desired. Additionally, the latch may be lifted up in order to facilitate engagement of the adaptor with the catheter.

The present invention also comprises a method for the attachment of a catheter which involves the steps of cannulating the blood vessel of a patient by piercing it with a needle or stylet, sliding the cannula of the catheter over the needle and into position within the vessel, withdrawing the needle leaving the catheter in place, connecting the IV tubing to the catheter by means of a snap-fit adaptor connection, connecting the catheter and tubing combination by means of a snap-fit engagement to an anchoring pad, peeling off the backing from a selfadhesive anchoring pad, applying the pad to the skin of the patient, forming a safety loop in the IV tubing, and attaching a portion of the loop by means of a friction engagement to the anchoring pad.

BRIEF DESCRIPTION OF THE DRAWINGS

FIG. 1 is a perspective view of a typical catheterization installation illustrating a stand, a container for fluid, a IV tubing and catheter.

FIG. 2 is a perspective view of the catheterization system of the present invention mounted on the back of a hand of a patient which is shown in phantom lines.

FIG. 3 is a partial perspective view illustrating the cannula of the catheter of the present invention being inserted into the skin of a patient over a previously inserted needle and adjacent the cut-out portion on the anchoring pad.

DETAILED DESCRIPTION OF THE INVENTION

Figures 4, 5:
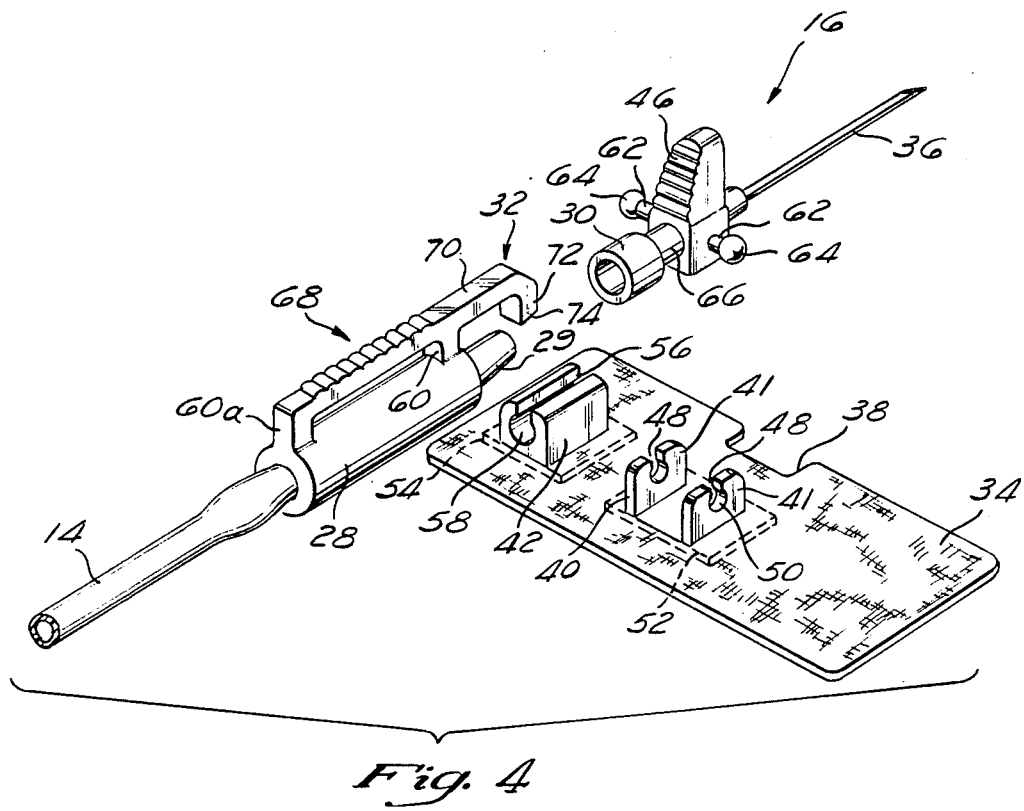
FIG. 4 is an exploded perspective view of the catheterization system of the present invention illustrating the anchoring pad, the catheter, and the tubing adaptor with its associated IV tubing.
FIG. 5 is a side view of the catheter and tubing adaptor illustrating the operation of the spring-actuated latch and activation mechanism.

FIG. 1 illustrates the basic set-up for a catheterization procedure, including a support stand 10, a container 12, a length of IV tubing 14, and the actual catheter 16 which is inserted into the patient. Typically, a patient is lying in a bed or is seated adjacent the stand 10. The stand is comprised of a pair of telescoping tubes 18 and 20 whose height can be adjusted by means of a set screw 22. The fluid 24 to be dispensed into the patient is maintained in the container 12 and is fed, either by gravity or by the pressure of the head of fluid above the patient, through the IV tubing 14 and catheter 16 and into the patient. The flow of the fluid 24 can be appropriately adjusted by means of a clamp (not shown) on the tubing 14.

FIG. 2 illustrates an enlargement of the catheterization system of the present invention and, in particular, the manner in which the IV tubing 14 is adapted to engage the catheter 16. The system is shown in position on the back of a hand of a patient which is shown in dot/dash lines, although the present invention can also be utilized for catheterization in other locations on the patient's body. In fact, the tubing/catheter connection which is particularly facilitated by the system of the present invention enables the system to be quickly installed on the patient and then modified without the loss of valuable time. The present invention provides a simple mechanism for accomplishing this interconnection without the time consuming use of surgical tape or the use of heavy, awkward mechanical devices found in the prior art.

FIG. 2 illustrates the distal end of the IV tubing formed in a safety loop 26 and engaging a tubing adaptor 28. The adaptor 28 is connected, by means of a cuff 30 and latch 32, to the catheter 16 which is in turn mounted on an anchoring pad 34. The cannula 36 of the catheter 16 is inserted under the skin of the patient, as illustrated in dotted lines in FIG. 2. A cut-out portion 38 on the pad 34, located adjacent the point of insertion, permits visual inspection of the catheterized site. The anchoring pad 34 is provided both with a bridge mechanism 40 for attachment of the catheter 16 and a slotted member 42 for receiving the safety loop 26 in the IV tubing 14. The anchoring pad 34 is mounted on the skin of a patient by means of a self-adhesive backing material. Prior to application, a non-stick surface is removed to reveal the self-adhesive backing which is then applied to the skin of the patient. For most catheterizations, this pad 34 is applied only once. Although the tubing 14 may be replaced every 24 to 48 hours, the anchoring pad 34 remains in place. Thus, there is no need to apply and remove surgical tape to the skin of the patient.

FIG. 3 illustrates the manner in which the catheter 16 is inserted into the patient. The anchoring pad 34, shown in dot-dash lines, may be first applied to the patient adjacent the location for insertion of the catheter 16, or may be applied after the catheter 16 is in place. A needle 44 or stylet is first inserted into the blood vessel at the desired point of insertion. The cannula 36 of the catheter 16 is then placed over the needle 44 which guides the cannula 36 into the skin and into position within the blood vessel. Once the cannula 36 is at the desired depth, as shown in FIG. 2, the needle 44 or stylet is removed, leaving the catheter 16 in place. The catheter 16 is then mounted on the bridge 40 of the anchoring pad 34 by means of a finger press 46, which extends substantially vertically upward from the catheter 16, in a manner described in more detail below.

FIGS. 4 and 5 illustrate the detailed construction of the various components of the catheterization system of the present invention. The distal end of the IV tubing 14 is integrally attached to the tubing adaptor 28 which is, in turn, attached to the catheter 16. This assembly is mounted on the anchoring pad 34 which is fixed to the skin of the patient. The anchoring pad 34 is provided with a bridge 40 comprising a pair of upright members 41 having slots 48 cut out of the upper surface thereof. The slots 48 are enlarged toward the center of the upright members 41 to form substantially circular seats 50. The upright members are mounted on the planar surface 52 of the bridge 40 which is embedded within the anchoring pad 34.

Preferably, the anchoring pad 34 is comprised of woven cloth material having a self-adhesive backing for attachment to the skin. Adjacent the bridge 40 is a slotted member 42 also having a flange-like base 54 embedded in the woven material comprising the anchoring pad 34. The slotted member 42 is provided with a narrow opening 56 which leads to a larger diameter orifice 58 having a circular configuration. The narrow opening 56 is designed to permit the insertion of the safety loop 26 respectively, into the orifice 58 upon application of gentle pressure, while providing retention for the loop within.

Referring to FIGS. 4 and 5, the catheter 16 is comprised of an elongate cannula 36 having a sharpened tip for insertion into the skin of the patient, a finger press 46 for mounting the catheter 16 on the pad 34, and a proximal cuff 30 for engagement with the tubing adaptor 28. The cannula 36 is preferably manufactured from a biologically-compatible material which is at the same time strong and durable. One suitable material is Teflon (a trademark of the DuPont Company). Extending laterally from the body of the catheter 16 is a pair of arms 62 having enlarged ends 64.

FIG. 2 and 5 illustrate the manner in which the catheter 16 is mounted on the bridge 40 of the anchoring pad 34. The arms 62 are inserted through the narrow slots 48 and into the seats 50 of the upright members 41 with the enlarged ends 64 preventing lateral movement thereof. In order to mount the catheter 16 on the anchoring pad 34, the arms 62 are brought into position in the slots 48 of the upright members 41. Upon the application of gentle downward pressure, which can be applied manually to the catheter 16 by means of the finger press 46, the arms 62 are snapped into the seats 50 of the upright members 41. The narrow opening of each slot 48 provides retention against upward removal forces, while the enlarged end 64 on each arm 62 prevents lateral movement of the catheter 16. Thus, the catheter 16 and its cannula 36 are securely maintained in position within the patient, and any injury or damage due to the movement of the catheter 16 is avoided by means of the interengagement with the bridge 40 on the anchoring pad 34. In order to remove the catheter 16, a gentle pressure in the opposite direction, upward, is all that is necessary to cause the arms 62 to pass through the narrow openings in the upright members 41 of the bridge 40. The bridge 40 is preferably constructed from a pliable polymer material, such as Delrin (a trademark), in order to provide this resiliency for the snap-fit.

It is important to note that the attachment of the catheter 16 to the bridge 40 of the anchoring pad 34 is accomplished by force or pressure applied in a direction substantially transverse to the length of the cannula 36. Thus, this attachment is accomplished without applying pressure to the point of insertion of the cannula 36 which could cause pain or discomfort to the patient. Likewise, the removal force is also in a transverse direction such that the patient is not likely to be injured. The bridge member 40 on the anchoring pad 34 also leaves the catheter 16 slightly elevated such that the fluid will continue to flow by gravity into the patient. In fact, the level of the seat 50 in the bridge member 40 is such that it provides a fixed level of inclination for the cannula 36 with respect to the plane of the patient's skin.

Just proximal of the body of the catheter 16 is a neck 66 of reduced diameter followed by a larger diameter cuff 30. The cuff 30 provides interconnection with the tubing adaptor 28 on a press-fit or friction-fit basis.

The tubing adaptor 28 is comprised of a cylindrical, handle-like body which fits comfortably in the hand of the user in order to facilitate its manipulation. The distal end 29 of the adaptor is comprised of a conical connector for frictional engagement with the cuff 30 of the catheter 16. Particularly, mounted longitudinally on one surface of the body is a latch 32 and activator mechanism 68 for securing the interengagement between the adaptor 28 and the catheter 16. The latch 32 is comprised of a distally-extending arm 70 and a hook member 72 which is substantially perpendicular to the arm 70. The latch 32 is mounted for articulation in a direction substantially transverse to the longitudinal dimension of the adaptor 28. This articulation is accomplished by an activator mechanism 68 which is secured at either end to the body of the adaptor 28 by means of posts 60 and 60a. This double post mounting for the activator 68 lengthens the life of the mechanism by avoiding premature failure due to fatigue. Preferably, the activator 68 is integral with the latch 32 and is also constructed from a pliable polymer material; however, other materials and configurations are equally possible. When pressure is applied manually to the activator 68, as shown in FIG. 5, the hook 72 of the latch 32 will move in an arc substantially transverse to the length of the adaptor 28. In accomplishing this substantially vertical, arcuate movement, illustrated in the plane of FIG. 5, the activator 68 and arm 70 behave essentially as a lever while the distal post 60 acts as a fulcrum.

Thus, in connecting the adaptor 28 to the catheter 16, the distal end 29 is first fitted within the cuff 30 and gentle pressure is applied to ensure a proper friction fit within the cuff. However, in order to secure this engagement, the hook 72 portion of the latch 32 is engaged in the reduced diameter neck 66 in order to prevent removal forces acting in a longitudinal direction from removing the adaptor 28 from the catheter 16. The interengagement between the latch 32 and the neck 66 may be accomplished in either one of two methods. First, the leading edge 74 of the hook 72 is tapered such that it will slide over the cuff 30 as engagement is made between the distal end 29 of the adaptor 28 and the cuff 30 Furthermore, the resiliency of the latch 32 permits it to spring upward in order to clear the cuff 30. Once the cuff 30 has been cleared, the hook 72 of the latch will snap down into the reduced diameter portion defined by the neck 66 in order to maintain the engagement. Alternatively, manual pressure may be applied to the activator 68 in order to lift the latch 32, to permit interengagement.

It should be pointed out that rotational movement of the adaptor 28 will not be imparted to the catheter 16 because of the nature of the engagement and the latch-/neck interconnection. This is an important advantage of the present invention in order to protect the patient from injury due to inadvertent movement of the catheter tubing 14 or adaptor 28.

Preferably, the tubing 14 is integrally attached to the adaptor in the molding process used to manufacture the adaptor 28; however, other suitable forms of attachment are conceivable.

The catheterization system of the present invention is also utilized in conjunction with a unique method for IV catheterization. First, the blood vessel of a patient is cannulated by piercing it with a needle 44. While holding the needle still, the catheter 16 is slided over the needle and into position within the vessel. The needle 44 is then carefully withdrawn and the catheter 16 is connected, by means of the spring-actuated latch 32, to the tubing adaptor 28. The latch 32 on the tubing adaptor 28 is snapped, either manually, or by virtue of the spring bias of the latch, into position on the neck 66 of the catheter 14 in order to secure it in thereto. The catheter/tubing adaptor combination is then press-fit into the bridge 40 on the anchoring pad 34 by means of the finger press 46, and the backing is peeled off of the pad. The pad 34 is then placed into position on the patient with the cut-out portion 38 adjacent the location of insertion of the catheter. A safety loop 26 is then formed in the tubing and is mounted on the slotted member 42 on the anchoring pad.

In conclusion, it can be seen that the catheterization system of the present invention greatly facilitates the accomplishment of this procedure on a patient by avoiding the necessity of using surgical tape. In fact, if conducted properly, no surgical tape is necessary whatsoever. Thus, a great deal of time is saved and the possible irritation of the patient's skin is avoided. Furthermore, the catheter tubing can be quickly and frequently changed without catheter disruption or irritation to the patient.

What is claimed is:

1. A catheterization system adapted for insertion into the arm, hand, or other location in the body of a patient for delivering fluids through a conduit to said patient, comprising:

a cannula for insertion into said patient at a particular location, said cannular passing said fluids into said patient, the proximal end of said cannula having means for receiving said conduit;

means for adapting said conduit for engagement with said receiving means on said cannula, said adapting means being rotatable with respect to said receiving means to relieve rotational forces in said conduit, said adapting means insulting said cannula from rotational movement of said conduit in order to avoid injury or discomfort to said patient; and means for mounting said cannula on said patient, said mounting means comprising snap-fit engagement means with said cannula for removably anchoring said cannula on said patient, said removable snap-fit engagement obviating the necessity for the time-consuming application of surgical tape or other apparatus, said adapting means being solely engageable and disengageable with said receiving means on said cannula in order to facilitate the frequent replacement of said conduit without requiring the removing of said cannula from said mounting means.

2. The catheterization system of claim 1, wherein said engagement means comprises means for substantially preventing longitudinal and lateral movement of said cannula with respect to said mounting means.

3. The catheterization of claim 1, wherein said mounting means comprises means for receiving a safety loop formed in said conduit to prevent movement in said conduit from passing directly to said adapting means.

4. The catheterization system of claim 1, wherein said mounting means further comprises self-adhesive means for attaching said mounting means to the body of said patient in a position adjacent the insertion location of said cannula.

5. The catheterization system of claim 1, wherein said mounting means further comprises means for permitting the visual inspection of said insertion location, and further permitting the application of antibiotic ointment to said location.

6. The catheterization system of claim 1, wherein said adapting means further comprises means for releasably maintaining said engagement of said cannula with said conduit, said maintaining means also insulating said cannula from rotational movement in said conduit.

7. The catheterization system of claim 6, wherein said maintaining means comprises an articulating latch for movement either (i) to a first position to permit engagement of said adapting means with said cannula or (ii) to a second position to permit removal of said adapting means from said cannula in order to permit the replacement of said conduit.

8. The catheterization system of claim 7, wherein said latch comprises a lever and a fulcrum, said lever being movable to said first position by means of manual pressure and being biased to automatically return to said second position.

9. The catheterization system of claim 8, wherein said lever of said latch is biased to said second position by means of the resiliency of said latch.

10. The catheterization system of claim 8, wherein said lever is provided with means for automatically activating said latch to said first position during engagement of said activating means on said latch with said cannula.

11. The catheterization system of claim 10 wherein said activating means comprises a tapered leading edge on said lever which urges said latch into said first position upon engagement of said leading edge with said cannula in order to provide said automatic activation of said latch.

12. The catheterization system of claim 7, wherein said latch is mounted at two locations on said adapting means.

13. The catheterization system of claim 1, wherein said cannula is provided with means for receiving manual pressure for guiding said cannula into position within said patient.

14. A catheterization system adapted for insertion into the arm, hand, or other location in the body of a patient for delivering fluids through a conduit to said patient, comprising:
  a cannula for insertion into said patient at a particular location, said cannula passing fluids into said patient;
  means for adapting said conduit for removable engagement with said cannula to permit frequent replacement of said conduit without removal of said cannula from said patient, said adapting means comprising means for rotationably engaging said cannula such that rotational forces on said conduit and said adapting means are not transmitted to said cannula in order to avoid pain and injury to said patient; and
  means for maintaining said removable rotatable engagement between said cannula and said adapting means, said maintaining means being selectively movable to a first positiom to permit said rotatable engagement between said adapting means and said cannula, and said maintaining means being automatically biased to a second postion to prevent removal of said adapting means from cannula,
  said adapting means being solely engageable and disengageable with said cannula to facilitate the frequent replacement of said conduit without requiring the removal of said cannula from said patient.

15. A catheterization system adapted for insertion into the arm, hand, or other location in the body of a patient for delivering fluids through a conduit to said patient, comprising:
  a cannula for insertion into said patient at a particular location, said cannula passing fluids into said patient, said cannula having a proximal cuff and neck of reduced diameter located distally with respect to said cuff;
  means for adapting said conduit for engagement with said cannula, said adapting means comprising a conical member for removable frictional engagement within said cuff of said cannula;
  means for retaining said removable frictional engagement between said conical member and said cuff, said retaining means comprising a lever removably engageable with said neck to prevent longitudinal forces on said adapting means from removing said frictional engagement, said retaining means being rotatable with respect to said neck so that rotational forces are not transmitted to said cannula in order to avoid pain and injury to said patient; and
  means for mounting said cannula on said patient, said adapting means being solely engageable and disengageable with said cannula but not engageable with said mounting means to facilitate the frequent replacement of said conduit without requiring the removal of said cannula from said mounting means, said cannula being rotatable with respect to said mounting means about an axis transverse to the longitudinal dimension of said cannula to facilitate the frequent detachment and replacement of said conduit.

16. The catheterization system of claim 15 further comprising:
  means for anchoring said catheterization system to said patient, said anchoring means comprising a self-adhesive backing to facilitate attachment to said patient, said anhoring means further comprising a pedestal; and
  means on said cannula for removable snap-fit engagement with said pedestal of said anchoring means, said cannula further comprising means for applying gentle manual pressure in a substantially transverse direction to said cannula in order to mount said cannula on said pedestal while avoiding pain and injury to said patient.

17. A method for catheterizing a patient comprising the steps of:
  a. Cannulating a blood vessel of a patient by means of a needle;
  b. Passing the cannula of catheter over said needle and into position within said blood vessel of said patient;
  c. Removing said needle from said patient;
  d. Manually acitvating a spring loaded retention latch mounted on a catheter tubing adapter to permit the frictional engagement of said catheter tubing adpater with said catheter, said frictional engagement being rotationally non-sensitive such that rotational forces applied to said tubing and said adapter are not transmitted to said catheter thereby avoiding discomfort and possible injury to said patient;
  e. Releasing said retention latch for removable engagement with a portion of said catheter to maintain the frictional engagement between said adapter and said catheter;
  f. Removably snap-fitting said catheter/adapter combination to an anchoring pad; and
  g. Mounting said anchoring paid to said patient by means of self-adhesive backing.

18. The method of claim 17 further comprising the step of placing the pad on the patient such that a cut-out portion on said pad is adjacent the point of insertion of said cannula.

19. An adapter for detachably mounting a conduit top a catheter for delivering fluids through said conduit and said catheter into the body of a patient, said catheter having a proximal cuff and an adjacent nec, comprising:
  an adapter body having proximal end attached to said conduit and a distal end for engagement with said catheter; and
  a latch mounted on said adapter body for rotational engagement with said neck of said catheter so that longitudinal engagement between said catheter and said adapter is maintained but rotational forces experienced by said adapter are not transmitted to said catheter, said longitudinal engagement being maintained by means of the engagement between said latch and said cuff, and said adapter being solely engageable and disengageable with said catheter to facilitate the frequent replacement of said conduit without requiring the removal of said catheter from said patient.

20. A catheterization system adapted for insertion into the arm, hand, or other location in the body of a patient for delivering fluids through a conduit to said patient, comprising:

a cannula for insertion into said patient at a particular location, said cannula passing fluids into said patient, the distal end of said cannula being inserted into said patient;

means on the proximal end of said cannula for rotatably receiving said conduit, said receiving means comprising a neck and a cuff proximally located with respect to said neck and having a larger diameter than that of said neck, said neck and said cuff locating said cannula with respect to said conduit while preventing rotational forces experienced by said conduit from being transmitted to said cannula to prevent pain and injury to said patient;

means on said proximal end of said cannula for mounting said cannula on said patient, said mounting means comprising a pair of lateral arms extending away from said cannula in a transverse direction to the longitudinal dimension of said cannula; and an anchoring pad having self-adhesive backing for attachment of said pad to said patient, said pad comprising a bridge for mounting said cannula on said patient, said bridge receiving said lateral arms of said cannula, said cannula being rotatable in said bridge about the axis through said lateral arms to facilitate the frequent replacement of said conduit without removal of said cannula form said patient.

* * * * *